US012359105B2

(12) United States Patent
Ye et al.

(10) Patent No.: US 12,359,105 B2
(45) Date of Patent: Jul. 15, 2025

(54) LOW TACK HOT-MELT PRESSURE SENSITIVE ADHESIVES

(71) Applicant: BOSTIK SA, Colombes (FR)

(72) Inventors: Xin Ye, Shanghai (CN); Peipei He, Guangdong (CN); Danfeng Li, Shanghai (CN)

(73) Assignee: BOSTIK SA, Colombes (FR)

( * ) Notice: Subject to any disclaimer, the term of this patent is extended or adjusted under 35 U.S.C. 154(b) by 745 days.

(21) Appl. No.: 17/617,999

(22) PCT Filed: Jul. 2, 2020

(86) PCT No.: PCT/EP2020/068618
§ 371 (c)(1),
(2) Date: Dec. 10, 2021

(87) PCT Pub. No.: WO2021/004870
PCT Pub. Date: Jan. 14, 2021

(65) Prior Publication Data
US 2022/0325149 A1 Oct. 13, 2022

(30) Foreign Application Priority Data

Jul. 5, 2019 (EP) ..................................... 19184785

(51) Int. Cl.
*C09J 153/02* (2006.01)
*C09J 7/38* (2018.01)
*C09J 11/08* (2006.01)

(52) U.S. Cl.
CPC ............. *C09J 153/02* (2013.01); *C09J 7/387* (2018.01); *C09J 11/08* (2013.01); *C09J 2400/263* (2013.01); *C09J 2453/00* (2013.01)

(58) Field of Classification Search
CPC .......... C08L 53/02; C08L 91/00; C08L 91/06; C09D 153/02; C09J 11/08; C09J 153/02; C09J 2400/263; C09J 2453/00; C09J 7/387

See application file for complete search history.

(56) References Cited

U.S. PATENT DOCUMENTS

| 7,442,739 | B1 | 10/2008 | Hatfield |
| 2010/0092703 | A1 | 4/2010 | Fouquay et al. |
| 2010/0193127 | A1 | 8/2010 | Fouquay et al. |

FOREIGN PATENT DOCUMENTS

| CN | 1726267 | A | | 1/2006 |
| CN | 104610892 | A | | 5/2015 |
| CN | 106471086 | A | | 3/2017 |
| EP | 0525251 | A1 | † | 2/1993 |
| EP | 0826380 | A2 | † | 3/1998 |
| EP | 1342765 | A2 | | 9/2003 |
| EP | 2178974 | B1 | | 11/2013 |
| EP | 3178896 | A1 | | 6/2017 |
| FR | 2912153 | A1 | | 8/2008 |
| FR | 2918069 | A1 | | 1/2009 |
| JP | H027955 | A | | 1/1990 |
| JP | 2017145425 | A | | 8/2017 |
| JP | 2018022194 | A | | 2/2018 |
| WO | 2004035705 | A2 | | 4/2004 |
| WO | 2006107763 | A2 | | 10/2006 |
| WO | WO2009026085 | A1 | | 2/2009 |
| WO | 2016004239 | A1 | | 1/2016 |
| WO | 2018145257 | A1 | † | 8/2018 |

OTHER PUBLICATIONS

Author Unknown, "Shellflex 371 Technical DataSheet Supplied by Shell Chemicals", Universal Selector by SpecialChem, Sep. 26, 2023, 2 pages.
ISA/EP; International Search Report and Written Opinion for International Patent Application No. PCT/EP2020/068618 dated Sep. 24, 2020, 8 pages.

† cited by third party

*Primary Examiner* — Ana L. Woodward
(74) *Attorney, Agent, or Firm* — NK Patent Law (57) ABSTRACT

The invention relates to a hot-melt pressure sensitive adhesive composition comprising at least one styrenic block copolymer, at least one tackifying resin, at least one mineral oil and from 4 to 15% by weight of at least one wax selected from the group consisting of paraffin waxes, Fischer-Tropsch waxes, ethylene-vinyl acetate waxes and any mixture thereof, based on the total weight of the hot-melt pressure sensitive adhesive composition. The invention also relates to an article comprising a surface coated with such a hot-melt pressure sensitive adhesive composition, to a use of such a hot-melt pressure sensitive adhesive composition and to a process for preparing such a hot-melt pressure sensitive adhesive composition.

17 Claims, 1 Drawing Sheet

LOW TACK HOT-MELT PRESSURE SENSITIVE ADHESIVES

CROSS-REFERENCE TO RELATED APPLICATIONS

This application is a U.S. National Stage application of International Patent Application No. PCT/EP2020/068618, filed on Jul. 2, 2020, which claims the benefit of European Patent Application No. 19184785.4, filed on Jul. 5, 2019.

TECHNICAL FIELD

The present invention relates to hot-melt pressure sensitive adhesive compositions, to processes of preparation thereof and to uses of such hot-melt pressure sensitive adhesive compositions.

TECHNICAL BACKGROUND

Hot-melt adhesives (HM adhesives) are substances which are solid at room temperature and which comprise neither water nor solvent. They are applied in the molten state after heating to a temperature generally of between 100 and 250° C., most often between 130 and 180° C., and solidify during cooling, thus forming a seal (or adhesive joint) which ensures the attachment of the two substrates to be assembled. Hot-melt adhesives are generally provided in the form of compositions which comprise a thermoplastic polymer and optionally a tackifying resin and a plasticizer. Among these HM adhesives, hot-melt pressure sensitive adhesives (HMPSA) are substances conferring an immediate tacky property (also called "tack") to a substrate coated with such adhesive which allows its instantaneous adhesion to another substrate under a slight and brief pressure, at room temperature.

HMPSA are broadly used in nonwoven applications and in particular for manufacturing disposable absorbent articles.

For example, document CN 104910841 describes a hot melt pressure sensitive adhesive (HMPSA) comprising 0-30% of a SBS (styrene-butadiene-styrene) elastomer, 0-30% of a SIS (styrene-isoprene-styrene) elastomer, 0-20% of an olefin copolymer, 0-70% of a first tackifying resin, 1-70% of a second tackifying resin, 10-30% of a mineral oil, 0-10% of a wax and 0.1-2% of an antioxidant.

Document FR 2912153 describes a HMPSA comprising a blend of SBS and SB (styrene-butadiene copolymer), a tackifying resin and a fatty acid.

Document FR 2918069 describes a HMPSA comprising a styrenic block copolymer (SBC), a tackifying resin and a carboxylic acid having a hydrocarbon chain comprising from 6 to 22 carbon atoms.

Document EP 3178896 relates to hot-melt adhesive compositions comprising a thermoplastic polymer chosen from polyolefins, styrenic block copolymers (SBC), ethylene-vinyl-acetate copolymers (EVA), and mixture thereof, a tackifying resin, an aldehyde scavenger, a plasticizer and an antioxidant.

Typically, HMPSAs have either high peel strength and high tack strength or low tack strength and low peel strength.

However, for some applications such as nonwoven applications, it may be desirable that the adhesive exhibits a low tack strength, while maintaining a high peel strength.

There is thus a need for hot-melt pressure sensitive adhesive compositions exhibiting both high peel performances and low tack strength.

SUMMARY OF THE INVENTION

It is a first object of the invention to provide a hot-melt pressure sensitive adhesive composition comprising at least one styrenic block copolymer, at least one tackifying resin, at least one mineral oil and from 4 to 15% by weight of at least one wax selected from the group consisting of paraffin waxes, Fischer-Tropsch waxes, ethylene-vinyl acetate waxes and any mixture thereof, based on the total weight of the hot-melt pressure sensitive adhesive composition.

In some embodiments, the at least one wax has a congealing point higher than or equal to 55° C.

In some embodiments, the at least one styrenic block copolymer is a styrene-butadiene-styrene copolymer, optionally in combination with a styrene-butadiene diblock copolymer, a styrene-isoprene-styrene copolymer, optionally in combination with a styrene-isoprene diblock copolymer, a styrene-ethylene-butylene-styrene copolymer, a styrene-butadiene-butylene-styrene copolymer, a styrene-ethylene-propylene-styrene copolymer or any mixture thereof.

In some embodiments, the amount of the at least one styrenic block copolymer is from 10 to 40% by weight based on the total weight of the composition.

In some embodiments, the at least one tackifying resin is chosen in the group consisting of natural and modified rosins, glycerol and pentaerythritol esters of natural and modified rosins, polyterpene resins, phenolic-modified terpene resins, aliphatic petroleum hydrocarbon resins having a Ring and Ball softening point of from about 60° C. to 140° C. and resulting from the polymerization of C5-hydrocarbon monomers, their hydrogenated derivatives, aromatic petroleum hydrocarbons resins having a Ring and Ball softening point of from about 60° C. to 140° C. and resulting from the polymerization of C9-hydrocarbon monomers, their hydrogenated derivatives, aliphatic and/or aromatic petroleum resins (C5/C9) having a Ring and Ball softening point of from about 60° C. to 140° C. and resulting from the polymerization of C5/C9-hydrocarbon monomers, their hydrogenated derivatives and any mixture thereof.

In some embodiments, the amount of the at least one tackifying resin is from 30 to 70% by weight based on the total weight of the composition.

In some embodiments, the at least one mineral oil is a naphthenic oil and/or a paraffinic oil, preferably a naphthenic oil.

In some embodiments, the amount of the at least one mineral oil is from 5 to 30% by weight based on the total weight of the composition.

In some embodiments, the hot-melt pressure sensitive adhesive composition further comprises one or more additives selected from the group consisting of antioxidants, fillers, surfactants, colorants, dyes, pigments, ultraviolet light stabilizers such as UV absorbers, fluorescent agents, pH indicators, rheology modifiers, cross-linking agents, and endblock reinforcing resins.

It is another object of the invention to provide an article comprising at least one interior or exterior surface coated with the hot-melt pressure sensitive adhesive composition as described above.

In some embodiments, the interior or exterior surface is a nonwoven surface, preferably comprising polypropylene, polyethylene, polyethylene terephthalate, cotton, bamboo, silk and/or polylactic acid.

In some embodiments, the article is a disposable diaper, disposable training pants, a disposable adult incontinent pad or brief, a disposable feminine sanitary napkin or pad.

It is another object of the invention to provide a use of the hot-melt pressure sensitive adhesive composition as described above for coating a surface.

In some embodiments, the surface is a nonwoven surface, preferably of a part of an article selected from disposable diapers, disposable training pants, disposable adult incontinent pads or briefs and disposable feminine sanitary napkins or pads.

It is another object of the invention to provide a process for preparing the hot-melt pressure sensitive adhesive composition as described above, comprising mixing the at least one styrenic block copolymer, the at least one tackifying resin, the at least one mineral oil and the at least one wax, in the molten state.

The present invention enables to meet the abovementioned need. In particular, the invention provides a hot-melt pressure sensitive adhesive composition exhibiting a low tack strength as well as a high peel performance. The HMPSA compositions according to the invention preferably also have good physical properties such as a softening point and a viscosity at 160° C. suitable for an use in nonwoven applications.

This is achieved by the presence in the HMPSA composition of a particular type of wax, chosen from the group consisting of paraffin waxes, Fischer-Tropsch waxes, ethylene-vinyl acetate waxes and their combinations, in a specific amount, namely from 4 to 15% by weight, based on the total weight of the HMPSA composition.

DETAILED DESCRIPTION

The invention will now be described in more detail without limitation in the following description.

Unless otherwise mentioned, the percentages in the present application are percentages by weight.

Styrenic Block Copolymer

The HMPSA of the invention comprises at least one styrenic block copolymer (SBC).

Styrenic block copolymers useful according to the invention include linear or radial block copolymers comprising at least one non elastomeric block A being a polystyrene block and at least one elastomeric block B being a totally or partially hydrogenated or a non-hydrogenated diene polymer block.

In particular, styrenic block copolymer according to the invention may be chosen from the following copolymers, and mixtures thereof:
  linear diblock copolymer of AB structure,
  linear triblock copolymer of ABA structure,
  radial block copolymers of the $(AB)_n Y$ structure,
wherein:
  A is a non-elastomeric polystyrene block,
  B is an elastomeric diene block polymer such as polybutadiene or polyisoprene block,
  Y is a multivalent compound, and
  n is an integer of at least 3.

The linear triblock copolymer of ABA structure may be used alone or in mixture with a linear diblock copolymer of AB structure.

The elastomeric block B can be post treated through partial or total hydrogenation to improve its heat stability.

Preferably, the styrenic block copolymer is chosen from the following linear triblock copolymers:
  styrene-butadiene-styrene copolymer (SBS) with or without styrene-butadiene diblock (SB),
  styrene-isoprene-styrene copolymer (SIS) with or without styrene-isoprene diblock (SI),
  styrene-ethylene-butylene-styrene copolymer (SEBS),
  styrene-butadiene-butylene-styrene copolymer (SBBS),
  styrene-ethylene-propylene-styrene copolymer (SEPS), and
  any mixture thereof.

More preferably, the styrenic block copolymer is a linear triblock copolymer of ABA structure, as defined above, and even more preferably a linear SIS or SBS triblock copolymer.

When the styrenic block copolymer is a mixture of linear triblock copolymer of ABA structure and linear diblock copolymer of AB structure, as defined above, the linear diblock content preferably ranges from 1 to 70% by weight relative to the total weight of the triblock and diblock mixture.

The amount of the end blocks A in the linear triblock copolymer of ABA structure, as defined above, may range from 14 to 51% by weight, preferably from 20 to 40% by weight, relative to the total weight of the linear triblock copolymer of ABA structure or, in the case of a mixture of linear triblock and diblock copolymers of ABA and AB structures, relative to the total weight of the triblock and diblock mixture.

Useful commercial styrenic block copolymers include KRATON D and G® series from KRATON POLYMERS, EUROPRENE Sol T® series from VERSALIS (ENI group), SOLPRENE® series from DYNASOL ELASTOMERS, and TAIPOL® and VECTOR® series from TSRC Corporation.

As examples of useful styrenic block copolymers, mention may be made of:
  KRATON® D1152 ES, a mixture of linear SBS triblock and SB diblock copolymers, with a styrene content of 29.5% by weight relative to the total weight of the mixture, an average molecular weight of around 122 000 g/mol, a MFI (measured according to ISO1133) of 8.5 grams (g)/10 minutes (min) at 200° C. under a load of 5 kilograms (kg), and a SB diblock content of around 17% by weight relative to the total weight of the mixture;
  KRATON® D1161, a mixture of linear SIS triblock and SI diblock copolymers, with a styrene content of 15% by weight relative to the total weight of the mixture, a MFI (measured according to ISO1133) of 9 g/10 min at 200° C. under a load of 5 kg, an average molecular weight of around 220 000 g/mol, and a SI diblock content of around 19% by weight relative to the total weight of the mixture;
  TAIPOL® SBS 4202 from TSRC Corporation, a linear SBS triblock copolymer with a styrene content of 40% by weight relative to the total weight of the triblock copolymer, a SB diblock content of less than 1%, a MFI (measured according to ASTM D1238) of 3-10 g/10 min at 190° C. under a load of 5 kg, an average molecular weight of around 102 400 g/mol;
  VECTOR® 4411 from TSRC Corporation, a linear SIS triblock copolymer with a styrene content of 44% by weight relative to the total weight of the triblock copolymer, a SI diblock content of less than 1%, a MFI (measured according to ASTM D1238) of 40 g/10 min at 200° C. under a load of 5 kg, an average molecular weight of around 106 000 g/mol:

VECTOR® 4213N from TSRC Corporation, a styrene-isoprene-styrene and styrene-isoprene (SIS/SI) block copolymer blend of a linear SIS triblock copolymer and about 25% of a SI diblock, with a styrene content of 25% by weight.

Advantageously, the styrenic block copolymer is present in an amount of from 10 to 40% by weight, based on the total weight of the HMPSA composition. More preferably, the HMPSA composition comprises from 15 to 30% by weight of styrenic block copolymer, based on the total weight of the HMPSA composition. In some embodiments, the HMPSA composition comprises from 10 to 15%, or from 15 to 20%, or from 20 to 25%, or from 25 to 30%, or from 30 to 35%, or from 35 to 40%, by weight, of styrenic block copolymer, based on the total weight of the HMPSA composition.

Tackifyinq Resin

The HMPSA composition of the invention also comprises at least one tackifying resin.

The tackifying resin may comprise one or several carbon-carbon double bond(s) or may comprise no carbon-carbon double bond. In this latter case, saturated tackifying resins may be prepared by total hydrogenation of unsaturated tackifying resins.

The tackifying resin is preferably selected among:
(a) natural and modified rosins such as, for example, gum rosins, wood rosins, tall-oil rosins, distilled rosins, hydrogenated rosins, dimerized rosins and polymerized rosins;
(b) glycerol and pentaerythritol esters of natural and modified rosins, such as, for example, the glycerol esters of pale wood rosin, the glycerol esters of hydrogenated rosin, the glycerol esters of polymerized rosin, the pentaerythritol esters of pale wood rosin, the pentaerythritol esters of hydrogenated rosin, the pentaerythritol esters of tall oil rosin and the phenolic modified pentaerythritol esters of rosin;
(c) polyterpene resins, including hydrogenated polyterpene resins having a Ring and Ball softening point of from about 20° C. to 140° C., the latter polyterpene resins generally resulting from the polymerization of terpene hydrocarbons, such as the monoterpene known as pinene, in the presence of Friedel-Crafts catalysts at moderately low temperatures;
(d) phenolic-modified terpene resins such as, for example, those resulting from the condensation, in an acidic medium, of a terpene and a phenol;
(e) aliphatic (including cycloaliphatic) petroleum hydrocarbon resins (C5) having a Ring and Ball softening point of from about 60° C. to 140° C., said resins resulting from the polymerization of C5-hydrocarbon monomers; and the corresponding hydrogenated derivatives resulting from a subsequent total or partial hydrogenation thereof;
(f) aromatic petroleum hydrocarbons resins (C9) having Ring and Ball softening point of from about 60° C. to 140° C., said resins resulting from the polymerization of C9-hydrocarbon monomers; and the corresponding hydrogenated derivatives resulting from a subsequent total or partial hydrogenation thereof;
(g) aliphatic (including cycloaliphatic) and/or aromatic petroleum resins (C5/C9) having a Ring and Ball softening point of from about 60° C. to 140° C., said resins resulting from the polymerization of C5/C9-hydrocarbon monomers; and the corresponding hydrogenated derivatives resulting from a subsequent total or partial hydrogenation thereof.

As examples of C5-hydrocarbon monomers useful to prepare the tackifying resins belonging to class (e) or (g), mention may be made of trans-1,3-pentadiene, cis-1,3-pentadiene, 2-methyl-2-butene, dicyclopentadiene, cyclopentadiene, cyclopentene, and any mixture thereof.

As examples of C9-hydrocarbon monomers useful to prepare the tackifying resins belonging to class (f) or (g), mention may be made of vinyltoluenes, dicyclopentadiene, indene, methylstyrene, styrene, methylindenes, and any mixture thereof.

A mixture of two or more of the above described tackifying resins may be used in the HMPSA composition according to the invention.

The tackifying resin used according to the invention may be a commercially available tackifying resin.

As examples of commercially available tackifying resins belonging to class (a), mention may be made of:
unmodified natural tall oil rosins from KRATON Company sold under the trade names SYLVAROS® (85, 90 and NCY);
the partially hydrogenated rosin from EASTMAN Company sold under the trade name FORALYN® E and the fully hydrogenated rosin from EASTMAN sold under the trade name FORAL® AX-E;
the dimerized rosin from EASTMAN Company sold under the trade name DYMEREX®.

As examples of commercially available tackifying resins belonging to class (b), mention may be made of:
SYLVALITE® RE 100L, a pentaerythritol based tall-oil rosin ester; and
SYLVALITE® RE 85L, a glycerol ester of tall oil rosin; both available from KRATON Company.

As examples of commercially available tackifying resins belonging to class (c), mention may be made of:
the polyterpene tackifiers from KRATON Company sold under the trade names SYLVAGUM® TR and SYLVARES® TR series (7115, 7125, A25L, B115, M1115).

As examples of commercially available tackifying resins belonging to class (d), mention may be made of:
the terpene phenol resins from KRATON Company sold under the trade names SYLVARES® TP (96, 2040, 300, 7042, 2019).

As examples of commercially available tackifying resins belonging to class (e), mention may be made of:
the aliphatic and cycloaliphatic petroleum hydrocarbon resins based on a C5-petroleum hydrocarbon fraction (such as a mixture of trans-1,3-pentadiene, cis-1,3-pentadiene, 2-methyl-2-butene, dicyclopentadiene, cyclopentadiene, cyclopentene), having a Ring and Ball softening point ranging from 60° C. to 140° C., from EASTMAN Company sold under the trade names WINGTACK® 98, WINGTACK® ET and from EXXONMOBIL sold under the trade name ESCOREZ® 1310LC;
the partially aliphatic and cycloaliphatic petroleum hydrocarbon resins based on a C5-petroleum hydrocarbon fraction (such as a mixture of trans-1,3-pentadiene, cis-1,3-pentadiene, 2-methyl-2-butene, dicyclopentadiene, cyclopentadiene, cyclopentene), having a Ring and Ball softening point ranging from 80° C. to 140° C., from KOLON Company sold under the trade names SUKOREZ® SU210 and SUKOREZ® 230; the softening point of SUKOREZ® SU210 is 110° C.;
the fully hydrogenated cycloaliphatic petroleum hydrocarbon resins based on a dicyclopentadiene-petroleum hydrocarbon fraction, having a Ring and Ball softening point ranging from 60° C. to 140° C., from EXXONMOBIL sold under the tradename ESCOREZ® 5400 series (5400, 5415, 5490); the softening point of ESCOREZ® 5400 is 100° C.

As examples of commercially available tackifying resins belonging to class (f), mention may be made of:

the aromatic petroleum hydrocarbon resins based on a C9-hydrocarbon petroleum fraction (such as a mixture of vinyltoluenes, dicyclopentadiene, indene, methylstyrene, styrene, methylindenes), having a Ring and Ball softening point of from about 60° C. to 140° C., available from KOLON INDUSTRIES sold under the trade names HIKOTACK® (P-90, P110 S and P120 S).

As examples of commercially available tackifying resins belonging to class (g), mention may be made of:

the partially hydrogenated cycloaliphatic modified aromatic petroleum hydrocarbon resins based on C5/C9-hydrocarbon petroleum fractions, having a Ring and Ball softening point of from about 60° C. to 140° C., from EXXONMOBIL Company sold under the tradename ESCOREZ® 5600 series (5600, 5615, 5690); the softening point of ESCOREZ® 5600 is 100° C.;

the non hydrogenated aliphatic modified aromatic hydrocarbon petroleum resin based on C5/C9-hydrocarbon petroleum fractions sold by ZEON under the trade name QUINTONE® DX390N, with a softening point of 93° C.;

DCPD (dicyclopentadiene) resins from Idemistu, sold under the trade names I-MARV P-125, which has a softening point of 120-130° C., and I-MARV S-100, which has a softening point of 95-105° C.

Preferably, the Ring and Ball (or softening point) of the tackifying resin lies in the range from 90° C. to 135° C., and even more preferably in the range from 90° C. to 130° C.

The softening temperature (or point) is determined in accordance with standard GB/T 15332-1994.

The total amount of tackifying resin is advantageously from 30 to 70% by weight based on the total weight of the HMPSA composition. Preferred ranges are from 35 to 65% by weight and from 40 to 60% by weight. In some embodiments, the HMPSA composition comprises from 30 to 35%, or from 35 to 40%, or from 40 to 45%, or from 45 to 50%, or from 50 to 55%, or from 55 to 60%, or from 60 to 65%, or from 65 to 70%, by weight, of tackifying resin, based on the total weight of the HMPSA composition.

Mineral Oil

The hot-melt pressure sensitive adhesive composition according to the invention comprises a mineral oil.

The mineral oil is preferably selected in the group consisting of naphthenic oils, paraffinic oils or any mixture thereof.

The mineral oil may be used as a plasticizer and may confer good processability to the hot-melt pressure sensitive adhesive composition. Moreover, the mineral oil may also provide desired viscosity control without substantially decreasing the adhesive strength or the service temperature (temperature of use) of the hot-melt pressure sensitive adhesive composition.

Naphthenic oils and paraffinic oils are petroleum based oils which consists in a mixture of naphthenic hydrocarbons (aliphatic, saturated or unsaturated, $C_4$ to $C_7$-member hydrocarbon rings, and preferably aliphatic, saturated or unsaturated, $C_4$ to $C_6$-member rings; by way of example, mention may be made of cycloalkanes such as cyclopentane, cyclohexane, cycloheptane), paraffinic hydrocarbons (saturated, linear or branched, alkanes) and aromatic hydrocarbons (aromatic hydrocarbon rings, which may be monocyclic or polycyclic, and preferably aromatic $C_6$-member hydrocarbon rings).

The classification of naphthenic and paraffinic oil is made based on the amount of each type of hydrocarbons in the oil. Typically, paraffinic oils have a paraffinic hydrocarbons content of at least 50% by weight; naphthenic oils have a naphthenic hydrocarbons content between 30% and 40% by weight, relative to the total weight of the mineral oil.

Preferably the mineral oil in the HMPSA composition according to the invention is a naphthenic oil.

The mineral oil may be a commercially available mineral oil. By way of example, mention may be made of the naphthenic oils from NYNAS sold under the trade names NYFLEX® 223 and NYFLEX® 222B or of the naphthenic oil from Karamay sold under the trade name KN4010.

The amount of mineral oil in the HMPSA composition is preferably from 5 to 30% by weight and more preferably from 10 to 25% by weight based on the total weight of the HMPSA composition. In some embodiments, the hot-melt pressure sensitive adhesive composition comprises from 5 to 10%, or from 10 to 15%, or from 15 to 20%, or from 20 to 25%, or from 25 to 30%, by weight, of mineral oil, based on the total weight of the HMPSA composition.

Wax

The HMPSA composition comprises from 4 to 15% by weight of at least one wax, based on the total weight of the composition. This wax is selected from the group consisting of paraffin waxes, Fischer-Tropsch waxes, ethylene-vinyl acetate (EVA) waxes and any mixture thereof.

By "paraffin wax" is meant a wax derived from crude oil. It generally consists of a complex mixture of hydrocarbons with the following general properties: nonreactive; nontoxic; good water barrier; clean-burning fuel; colorless. Paraffin waxes are characterized by a clearly defined crystal structure. The melting point of paraffin waxes generally falls between about 43 and about 71° C. Paraffin waxes often contain a large amount of straight-chain hydrocarbons, and can also contain branched hydrocarbons, such as isoparaffins and other branched materials, and cycloalkanes, such as cycloparaffins and other cyclo-containing materials.

By "Fischer-Tropsch wax" is meant a wax obtained by the so-called Fischer-Tropsch process. The Fischer-Tropsch process includes converting a synthesis gas comprising mainly hydrogen and carbon monoxide to hydrocarbons. The conversion is effected by contacting the synthesis gas with a Fischer-Tropsch catalyst, normally an iron or cobalt based catalyst, in a fixed bed or a slurry bed reactor under either low or high temperature Fischer-Tropsch operating conditions. In this manner, a mixture of hydrocarbons having different boiling ranges is obtained. The Fischer-Tropsch wax is then recovered, e.g. by means of distillation, from this hydrocarbon mixture. The Fischer-Tropsch wax typically has a composition wherein about 80% by volume thereof has a boiling point higher than 550° C. atmospheric equivalent temperature ("AET").

By "EVA wax" is meant oligomeric polymer compounds that are prepared via a process comprising the co-polymerization of ethylene monomers and vinyl acetate monomers and that have the following properties: (a) solid at room temperature; (b) low melting point; and (c) insoluble in water. The EVA copolymers of the EVA wax may be functionalized or modified in any possible manner.

Advantageously, the wax may have a congealing point higher than or equal to 55° C., preferably higher than or equal to 58° C. The congealing point may be determined according to ASTM D3954. Using a wax having such a congealing point may make it possible to further decrease the tack strength of the HMPSA composition.

The wax according to the invention may be a commercially available wax. Examples of commercially available waxes suitable for the present invention include Fischer-Tropsch waxes from Shell sold under the trade names SX605, which has a congealing point of 58-62° C., SX705, which has a congealing point of 67-72° C., SX805, which has a congealing point of 78-85° C. and SX105, which has a congealing point of 101-108° C., and from Sasol sold under the trade name C-80M, which has a congealing point of 80-85° C. Other examples are 64 #paraffin wax from Sinopec, having a melting point of 64-66° C. and the EVA wax from Honeywell sold under the trade name AC-400A, having a vinyl acetate content of 13% by weight, a dropping point of 92° C. and a viscosity at 140° C. of 595 mPa·s.

Preferably, the HMPSA composition comprises from 4.5 to 13%, more preferably from 5 to 10%, by weight of wax, based on the total weight of the HMPSA composition. In some embodiments, the HMPSA composition comprises from 4 to 5%, or from 5 to 6%, or from 6 to 7%, or from 7 to 8%, or from 8 to 9%, or from 9 to 10%, or from 10 to 11%, or from 11 to 12%, or from 12 to 13%, or from 13 to 14%, or from 14 to 15%, by weight of wax, based on the total weight of the HMPSA composition.

Other Additives

The HMPSA composition of the invention may comprise one or more other additives. In particular, the HMPSA composition may comprise one or more additives selected from the group consisting of antioxidants, fillers, surfactants, colorants, dyes, pigments, ultraviolet light stabilizers such as UV absorbers, fluorescent agents, pH indicators, rheology modifiers, cross-linking agents and endblock reinforcing resins. The HMPSA may comprise other additives commonly used in adhesive compositions.

Preferably, these other additives are present in the HMPSA composition in an amount of from 0.1 to 20% by weight, based on the total weight of the composition, for example from 0.1 to 0.5%, or from 0.5 to 1%, or from 1 to 2%, or from 2 to 5%, or from 5 to 10%, or from 10 to 15%, or from 15 to 20%, by weight.

Advantageously, the HMPSA composition according to the invention may comprise at least one antioxidant.

The antioxidant is preferably incorporated in the HMPSA composition to help to protect the hot melt adhesive composition from chemical degradations. Said degradations generally involve the reactions of free radicals, resulting from chain scission catalyzed either by ultraviolet light or heat, with dioxygen. Such degradation is usually manifested by a deterioration in the appearance (browning of color) or other physical properties of the adhesive, and in the performance characteristics of the adhesive.

In particular, the antioxidant may protect the HMPSA composition from the effect of thermal degradation reactions that mainly occur during the manufacturing and application process of the HMPSA, where the HMPSA composition and its ingredients are typically heated for a long time at high temperature in presence of dioxygen.

Useful antioxidants include hindered phenols and sulfur and phosphorus containing phenols. Hindered phenols are well known to those skilled in the art and may be characterized as phenolic compounds which also contain sterically bulky groups in close proximity to the phenolic hydroxyl group thereof. In particular, tertiary butyl groups are generally substituted onto the benzene ring in at least one of the ortho positions relative to the phenolic hydroxyl group.

Representative hindered phenols include:
1,3,5-trimethyl-2,4,6-tris(3-5-di-tert-butyl-4-hydroxybenzyl) benzene;
pentaerythritol tetrakis(3-(3,5-di-tert-butyl-4-hydroxyphenyl) propionate);
n-octadecyl-3(3,5-di-tert-butyl-4-hydroxyphenyl) propionate;
4,4'-methylenebis(4-methyl-6-tert-butylphenol);
4,4'-thiobis(6-tert-butyl-o-cresol);
2,6-di-tert-butylphenol;
6-(4-hydroxyphenoxy)-2,4-bis(n-octylthio)-1,3,5-triazine;
2,4,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate;
sorbitol hexa-(3,3,5-di-tert-butyl-4-hydroxy-phenyl) propionate;
2,2'-methylene bis(4-methyl-6-tert-butylphenol)phosphites including, e.g. tris-(p-nonylphenyl)-phosphite (TN PP) and bis(2,4-di-tert-butylphenyl)4,4'-diphenylenediphosphonite, di-stearyl-3,3'-thiodipropionate (DSTDP);
tetrakis(methylene(3,5-di-ter-butyl-4-hydroxyhydrocinnamate)) methane;
tris(2,4-di-tert-butylphenyl)phosphate; and combinations thereof.

The hindered phenol antioxidants may be used by themselves or in combination with other antioxidants, such as phosphites antioxidants like IRGAFOS® series, or aromatic amine antioxidants like NAUGARD® series from ADDIVANT.

Useful antioxidants may be commercially available under a variety of trade designations including, e.g., the hindered phenolic antioxidants of IRGANOX® series from BASF including, e.g., IRGANOX® 1010 (tetrakis(methylene(3,5-di-ter-butyl-4-hydroxyhydrocinnamate))methane) and IRGAFOS® 168 antioxidant (tris(2,4-ditert-butylphenyl) phosphate). Another example is CHINOX® 1010 (pentaerythritol tetrakis(3-(3,5-di-tert-butyl-4-hydroxyphenyl) propionate)) from Shuangjian.

The total amount of antioxidant in the HMPSA composition is preferably from 0.1 to 3% by weight, more preferably from 0.1 to 2% by weight, and even more preferably from 0.5 to 1% by weight, based on the total weight of the HMPSA composition.

The performance of the antioxidants useful according to the invention may be further enhanced by utilizing, in conjunction therewith: (1) synergists such as, for example, thiodipropionate esters and phosphites; and/or (2) chelating agents and metal deactivators like, for example, ethylenediamine tetraacetic acid, salts thereof, and disalicylalpropylenediimine.

Other optional ingredient(s) may be incorporated into the HMPSA composition according to the invention in order to modify some of its physical properties.

Among the optional ingredients, mention may be made of fillers, surfactants, colorants, dyes, pigments, ultraviolet light stabilizers such as UV absorbers, fluorescent agents, pH indicators, rheology modifiers cross-linking agents, and the like. The total amount of these optional ingredient(s) may range from 0 to 10% by weight, preferably from 0.1 to 5% by weight, and more preferably from 0.1 to 2% by weight, based on the total weight of the HMPSA composition.

The HMPSA composition may also comprise a least one endblock reinforcing resin, especially when the hot melt adhesive composition according to the invention is intended to be used for a highly demanding application which requires a high cohesion of the adhesive joint bonding two assembled substrates.

The endblock reinforcing resin is primarily an aromatic resin based on pure or mixed monomer streams of aromatic monomers. Typical examples of such aromatic monomers include aromatic C9-hydrocarbon monomer, styrene, alpha-methyl styrene, vinyl toluene. Preferred are those based on alpha-methyl styrene.

Useful endblock reinforcing resins may be commercially available under a variety of trade names including, e.g., PLASTOLYN® series from EASTMAN CHEMICAL The endblock reinforcing resin used according to the invention may have a molecular weight of from 5000 to 15000 g/mol.

The Ring and Ball softening point of the aromatic endblock resin preferably ranges from 90° C. to 160° C., more preferably from 100° C. to 140° C., and even more preferably from 120° C. to 140° C.

When the endblock reinforcing resin is present in the HMPSA composition according to the invention, its total amount preferably ranges from 3 to 20% by weight, and more preferably from 5 to 15% by weight, based on the total weight of the HMPSA composition.

Process for Preparing the HMPSA Composition

The invention also relates to a process for preparing the hot-melt pressure sensitive adhesive composition as described above.

The HMPSA composition may be prepared by mixing the at least one styrenic block copolymer, the at least one tackifying resin, the at least one mineral oil and the at least one wax, in the molten state. Optional other ingredients or additives of the composition, as described above, may be mixed with the abovementioned components.

The hot-melt pressure sensitive adhesive composition of the present invention may be produced using any of the techniques known in the art. Preferably, the step of mixing is carried out at a temperature of from 140 to 170° C. The ingredients are preferably mixed for at least several hours, typically at least 4 hours, and preferably from 4 to 6 hours.

The HMPSA composition according to the invention can be prepared in presence of dioxygen (such as under air atmosphere), or preferably under inert atmosphere e.g. under carbon dioxide or nitrogen to limit potential degradation by oxidative reactions.

According to preferred embodiments, the process for preparing the HMPSA composition according to the invention comprises:
 a first step of mixing the tackifying resin and the mineral oil, preferably with the antioxidant when present, at a temperature ranging from 120° C. to 140° C., at least for a period of time long enough to melt all the tackifying resin,
 a second step of adding the styrenic block copolymer into the mixture obtained in the previous step under stirring and heating at a temperature ranging from 150° C. to 170° C., at least for a period of time long enough to melt all the styrenic block copolymer,
 the wax being possibly added either during the first step or during the second step in mixture with the other ingredients, or subsequently during a subsequent third step in the composition resulting from the second step at a temperature ranging from 130° C. to 150° C. under stirring.

Preferably, the wax is added in the third step.

In other embodiments, the process for preparing the HMPSA composition according to the invention comprises:
 a first step of melting and mixing the styrenic block copolymer and the mineral oil;
 a second step of adding the tackifying resin into the mixture obtained in the previous step, under stirring,
 the wax being possibly added either during the first step or during the second step in mixture with the other ingredients, or subsequently during a subsequent third step in the composition resulting from the second step, under stirring.

Additionally, the process of the invention may comprise a step of applying vacuum to remove any entrapped air in the mixture, before or after any of the steps of process described previously.

Other useful optional ingredients or additives which may be present in the HMPSA composition according to the invention, as described above, may be added at any step of the process according to the invention.

The HMPSA composition according to the invention, preferably prepared by the above described process may further be kept, for example in a melting kettle, under melted state for up to an additional 15 hours before being cooled down and packaged in form of a ready-to-use solid composition.

Use

The invention also relates to the use of the hot-melt pressure sensitive adhesive composition as described above, for coating a surface.

The surface to be coated may comprise nonwoven fabric, tissue, absorbent fluff, super absorbent polymer (SAP), composite material, plastics which may be elastomeric or non-elastomeric, for example styrenic block copolymers (SBC), polyurethane, and polyolefin, and any mixture thereof. In particular embodiments, the surface is a nonwoven surface. More preferably, the surface comprises polypropylene (PP), polyethylene (PE), polyethylene terephthalate (PET), cotton, bamboo, silk and/or polylactic acid.

The invention also relates to the use of the hot-melt pressure sensitive adhesive composition as described above, for bonding two substrates.

The present application relates to a process of manufacturing an assembly product (or laminate) comprising:
 a step (i) of heating at a temperature ranging from 130° C. to 180° C. the HMPSA composition according to the invention, for at least a period of time long enough to render the hot melt adhesive composition liquid enough to be applied on a substrate (for example at least two hours), then
 a step (ii) of coating said composition on a first substrate, then
 a step (iii) of putting into contact the coated surface of the first substrate with the surface of a second substrate, so as to form an adhesive joint bonding the two substrates.

The substrates may be different or of same nature, with various forms (layer or film, strands, fluff).

Preferably, each substrate may be chosen independently from one another among nonwoven fabric, tissue, absorbent fluff, super absorbent polymer (SAP), composite material, plastics which may be elastomeric or non-elastomeric, and which may be chosen for example from styrenic block copolymers (SBC), polyurethane, and polyolefin, and any mixture thereof.

The composite material may be made of at least one of the above-mentioned materials.

The HMPSA composition according to the invention may be coated or applied with a variety of application techniques known in the art, which include contact type application (such as slot die coating) and non-contact type application (such as spraying or fiberization).

In particular, as mentioned above, the HMPSA composition according to the invention may easily be applied through conventional coating nozzles, such as those having a diameter from 0.305 to 0.762 mm or a slot die length adjustable by a shim and ranging from 20 μm to 300 μm.

The amount of coated adhesive by surface unit can vary in a very large range, for example from 0.1 to 50 gsm (gram by square meter), depending on the substrates intended to be bonded. For example, a range from 0.2 to 1 gsm may be used in case of nonwoven substrates bonded with a polyethylene film to produce a cloth-like backsheet assembly, while a range from 3 to 7 gsm may be used in case of the assemblies of disposable multilayers. A much higher range, from 20 to 40 gsm, may also be used when high shear performance is requested, like for instance for bonding ears to the diaper chassis.

Before being applied on the surface of the first substrate, the HMPSA composition may further be kept in a melting kettle for up to 4 days.

The HMPSA composition according to the invention can be applied on a substrate or stored in presence of dioxygen (under air atmosphere), or preferably under inert atmosphere to limit degradations due to oxidative reactions.

According to another aspect, the invention relates to an article comprising at least one interior or exterior surface coated with the hot-melt pressure sensitive adhesive composition as described above. In particular embodiments, the present invention relates to an assembly product comprising at least two substrates bonded by at least one HMPSA composition according to the invention.

The coated surface and the bonded substrates may be as described above.

The HMPSA composition according to the invention may be used as the laminating adhesive to bind a plurality of substrate layers for example to manufacture toilet tissues, paper towels, wipes and other consumer products, particularly absorbent articles such as disposable hygiene products, and more particularly disposable diapers.

In some embodiments, the assembly product according to the invention may be a multilayer product comprising at least two layers of substrate(s) bonded by at least one HMPSA according to the invention.

In the assembly product according to the invention, the at least two layers of substrate(s) may be joined adhesively by a layer of HMPSA composition according to the invention, in sandwich between the two layers of substrate(s).

Alternatively or cumulatively, the at least two layers of substrate(s) may be joined adhesively by spots of HMPSA composition according to the invention.

Preferably, the article/assembly product is a disposable nonwoven absorbent article. Mention can be made of disposable diapers, disposable training pants, disposable adult incontinent pads or briefs and disposable feminine sanitary napkins or pads.

EXAMPLES

The following examples illustrate the invention without limiting it.

Raw Materials Used in the Examples

The components used in the examples are described in the table below.

| Component | Features | Function |
|---|---|---|
| Mineral oil | Kinematic viscosity at 40° C.: 155.3 mm$^2$/s | Naphthenic oil, plasticizer |
| Antioxidant | | Antioxidant |
| Polymer 1 | Linear; 40 wt. % of polystyrene (PS) | SBS, polymer |
| Polymer 2 | 25 wt. % of polystyrene (PS); 25 wt. % of diblock | SIS/SI blend, polymer |
| Resin 1 | Softening point: 120-130° C. | DCPD, tackifying resin |
| Resin 2 | Softening point: 95-105° C. | DCPD, tackifying resin |
| Wax 1 | Congealing point: 58-62° C. | Fischer-tropsch (FT) wax, synthetic paraffin wax |
| Wax 2 | Congealing point: 67-72° C. | FT wax, synthetic paraffin wax |
| Wax 3 | Congealing point: 101-108° C. | FT wax |
| Wax 4 | Congealing point: 80-85° C. | FT wax |
| Wax 5 | Melting point: 64-66° C. | Paraffin wax |
| Wax 6 | VA (vinyl acetate) content: 13 wt. %; Mettler drop point: 92° C.; Viscosity at 140° C.: 595 mPa·s; | EVA wax, Ethylene-Vinyl Acetate copolymers |
| Wax 7 | Mettler drop point: 113° C.; Viscosity at 140° C.: 450 mPa·s | Polyethylene homopolymers wax |
| Wax 8 | Mettler drop point: 140° C.; Viscosity at 150° C.: 8500 mPa·s | High-density oxidized polyethylene homopolymers wax |

The congealing point and the Mettler drop point of the waxes may be determined according to ASTM D3954, the melting point may be measured according to GB/T 2539.

Test Methods

Figure 1:
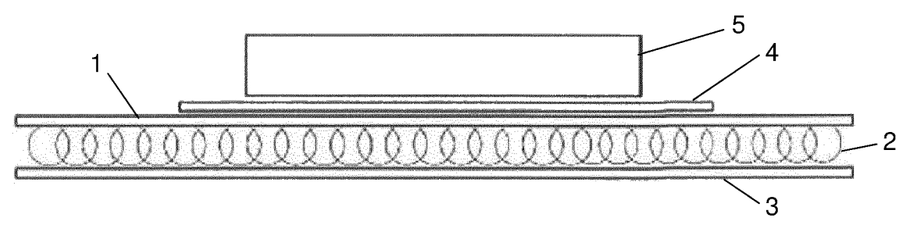
FIG. 1 shows a diagram of the structure made to measure the tack strength of a hot-melt pressure sensitive adhesive composition as described in the examples.

The following measurement methods are used:

softening point is measured according to standard GB/T 15332-1994.

viscosity is measured according to standard HG/T 3660-1999.

peel strength is measured according to standard GB/T 2792-1998, according to the following method:
1) A lamination sample comprising the tested HMPSA composition between a primary substrate, which is a SMS (spunbond/meltblown/spunbond) nonwoven fabric, and a secondary substrate, which is a hydrophilic nonwoven fabric, is made.
2) The laminated sample is left 24 h.
3) The peel strength is measured according to standard GB/T 2792-1998; the maximum force is recorded as the peel strength.

tack strength is measured according to standard GB/T 2792-1998, according to the following method:
1) A lamination sample comprising the tested HMPSA composition between a primary substrate, which is a SMS nonwoven fabric, and a secondary substrate, which is a release film, is made.
2) The release film is removed.
3) As show in FIG. 1, a hydrophilic nonwoven fabric 1 is put on the HMPSA layer 2 coated on the SMS nonwoven fabric 3; then a polyethylene plate 4 and a load 5 of 300 g are placed on this assembly.
4) This structure is then placed in an oven at 40° C. for 24 h.
5) The structure is cooled down to room temperature.
6) Peel strength is measured according to GB/T 2792-1998 (the peel strength being the maximum force) and recorded as the tack strength.

In the peel strength test and in the tack strength test, experiments are carried out for each HMPSA composition. The coating conditions used for each of these experiments are the following:

| Experiment | Application nozzle | Substrates: Primary/Secondary | Temperature (° C.) | Hot air (° C.) | Width (mm) | Add-on (g/m$^2$) | O.T. (s) |
|---|---|---|---|---|---|---|---|
| 1 (peel strength test) | Summit ™ nozzle | SMS nonwoven/ Hydrophilic nonwoven | 170 | 170 | 50 | 4 | 0.8 |
| 2 (tack strength test) | Summit ™ nozzle | SMS nonwoven/ Release paper | 170 | 170 | 50 | 6 | 0.8 |

SMS = spunbond/meltblown/spunbond
"Temperature" is the temperature of the tank containing the adhesive composition to be applied.
"Width" is the width of the coating of the HMPSA on the primary substrate.
"Add-on" is the amount of HMPSA coated on the primary substrate.
"O.T." stands for opening time, which is the time that the HMPSA coated on the primary substrate takes to travel from the nozzle to the compression zone where the secondary substrate is applied on the HMPSA.

Example 1

A first round (round 1) of experiments was performed.

Preparation of the Compositions

The components of the compositions used in round 1 and their amount (in parts by weight) are the following:

| Composition | C-1 | C-2 | C-3 | C-4 | C-5 | C-6 | C-7 | C-8 | C-9 | C-10 | C-11 |
|---|---|---|---|---|---|---|---|---|---|---|---|
| Mineral oil | 20 | 20 | 20 | 20 | 20 | 20 | 20 | 20 | 20 | 20 | 20 |
| Antioxidant | 0.5 | 0.5 | 0.5 | 0.5 | 0.5 | 0.5 | 0.5 | 0.5 | 0.5 | 0.5 | 0.5 |
| Polymer 1 | 6 | 6 | 6 | 6 | 6 | 6 | 6 | 6 | 6 | 6 | 6 |
| Polymer 2 | 17.5 | 17.5 | 17.5 | 17.5 | 17.5 | 17.5 | 17.5 | 17.5 | 17.5 | 17.5 | 17.5 |
| Resin 1 | 30 | 30 | 30 | 30 | 30 | 30 | 30 | 30 | 30 | 30 | 30 |
| Resin 2 | 26 | 26 | 26 | 26 | 26 | 26 | 26 | 26 | 26 | 26 | 26 |
| Wax 4 | | 5 | 10 | | | | | | | | |
| Wax 7 | | | | 3 | 5 | 10 | | | | | |
| Wax 5 | | | | | | | | 8 | | | |
| Wax 1 | | | | | | | 3 | | | 15 | 20 |
| Wax 2 | | | | | | | | | | | 3 |

The abovementioned compositions were prepared by mixing the melt styrenic block copolymers with the mineral oil and the antioxidant, then the tackifying resin was added under stirring and the wax is added in a third step under stirring. C-1 is a typical HMPSA composition for nonwoven applications. C-2, C-3, C-7 and C-9 are HMPSA compositions according to the invention. C-1, C-4, C-5, C-6, C-8, C-10 and C-11 are comparative compositions.

The properties of the compositions were measured as described above.

Results

The average peel strengths of the HMPSA compositions are shown in the table below:

| HMPSA composition | Peel strength (average) (N/25 mm) | Standard deviation (N/25 mm) |
|---|---|---|
| C-1 | 2.51 | 0.45 |
| C-2 | 3.55 | 0.67 |
| C-3 | 2.08 | 0.39 |
| C-4 | 3.25 | 0.30 |
| C-5 | 3.60 | 0.80 |
| C-6 | 1.54 | 0.13 |
| C-7 | 3.41 | 0.41 |
| C-8 | 4.03 | 0.54 |
| C-9 | 2.48 | 0.12 |
| C-10 | 1.51 | 0.14 |
| C-11 | 2.44 | 0.24 |

The average tack strengths of the HMPSA compositions are shown in the table below:

| HMPSA composition | Tack strength (average) ($\times 10^{-3}$ N/25 mm) | Standard deviation ($\times 10^{-3}$ N/25 mm) |
|---|---|---|
| C-1 | 543 | 50 |
| C-2 | 368 | 64 |
| C-3 | 75 | 21 |
| C-4 | 718 | 33 |
| C-5 | 765 | 220 |
| C-6 | 192 | 28 |
| C-7 | 317 | 39 |
| C-8 | 804 | 112 |
| C-9 | 82 | 9 |
| C-10 | 78 | 10 |
| C-11 | 627 | 87 |

Compared to the typical HMPSA composition C-1, compositions C-2, C-3, C-7 and C-9 exhibit a higher peel strength or a quite similar peel strength (in case of composition C-3), as well as a lower tack strength.

Comparative compositions C-4, C-5, C-8 and C-11 also exhibit a higher or similar peel strength to that of composition C-1 but have a much higher tack strength.

Comparative compositions C-6 and C-10 have a lower tack strength than that of composition C-1 but exhibit a much lower peel strength.

Therefore, compositions C-2, C-3, C-7 and C-9 according to the invention exhibit both a high peel strength and a low tack strength.

Round 2

A second round (round 2) of experiments was performed.

Preparation of the Compositions

The components of the compositions used in round 2 and their amount (in parts by weight) are the following:

| Composition | C-1a | C-12 | C-13 | C-14 | C-15 | C-16 |
|---|---|---|---|---|---|---|
| Mineral oil | 20 | 20 | 20 | 20 | 20 | 20 |
| Antioxidant | 0.5 | 0.5 | 0.5 | 0.5 | 0.5 | 0.5 |
| Polymer 1 | 6 | 6 | 6 | 6 | 6 | 6 |
| Polymer 2 | 17.5 | 17.5 | 17.5 | 17.5 | 17.5 | 17.5 |
| Resin 1 | 30 | 30 | 30 | 30 | 30 | 30 |
| Resin 2 | 26 | 26 | 26 | 26 | 26 | 26 |
| Wax 3 | | 5 | | | | |
| Wax 2 | | | 10 | | | |
| Wax 6 | | | | 10 | | |
| Wax 8 | | | | | 5 | 10 |

The abovementioned compositions were prepared and tested in the same manner as in round 1, except that ambient temperature during the coating of the HMPSA compositions was higher in round 2 than in round 1.

C-12, C-13, and C-14 are HMPSA compositions according to the invention. C-1a, C-15 and C-16 are comparative compositions.

Results

The average peel strengths of the HMPSA compositions are shown in the table below:

| HMPSA composition | Peel strength (average) (N/25 mm) | Standard deviation (N/25 mm) |
|---|---|---|
| C-1a | 3.63 | 0.48 |
| C-12 | 3.49 | 0.79 |
| C-13 | 3.59 | 0.74 |
| C-14 | 3.57 | 0.50 |
| C-15 | 3.15 | 0.80 |
| C-16 | 2.54 | 0.29 |

The average tack strengths of the HMPSA compositions are shown in the table below:

| HMPSA composition | Tack strength (average) ($\times 10^{-3}$ N/25 mm) | Standard deviation ($\times 10^{-3}$ N/25 mm) |
|---|---|---|
| C-1a | 237 | 49 |
| C-12 | 146 | 50 |
| C-13 | 140 | 40 |
| C-14 | 82 | 14 |
| C-15 | 301 | 17 |
| C-16 | 277 | 63 |

Composition C-1a is the same composition as composition C-1 in round 1 but it exhibits different properties since ambient temperature was different during the coating of C-1 and C-1a for the tests (room temperature affects the wetting process of the adhesives: the higher the room temperature, the better the wetting process and the higher the peel strength).

Compared to the typical HMPSA composition C-1a, compositions C-12, C13 and C-14 exhibit a similar peel strength. However, these compositions also exhibit a much lower tack strength than that of composition C-1a.

Comparative compositions C-15 and C-16 have a lower peel strength than that of composition C-1a. In addition, compositions C-15 and C-16 exhibit a higher tack strength compared to that of composition C-1a.

Therefore, compositions C-12, C-13 and C-14 according to the invention exhibit both a high peel strength and a low tack strength.

Example 3

The above compositions C-1 and C-2 to C-16 were also tested for other properties. The results are shown in the table below:

| Composition | Viscosity at 160° C. (mPa·s) | Softening point (° C.) | Tx (° C.) | Tg (° C.) | Tanδ at Tg | Mini valley | G' at 24° C. | G' at 40° C. |
|---|---|---|---|---|---|---|---|---|
| C-1 | 4500 | 100 | 97.3 | 25.9 | 1.116 | 0.288 | $3.27 \times 10^6$ | $4.42 \times 10^5$ |
| C-2 | 3200 | 100.2 | 96.2 | 22.0 | 1.380 | 0.180 | $1.07 \times 10^6$ | $2.23 \times 10^5$ |
| C-3 | 2158 | 97.5 | 95.5 | 21.9 | 1.020 | 0.169 | $2.01 \times 10^6$ | $4.65 \times 10^5$ |
| C-4 | 5342 | 104.2 | 100.0 | 22.0 | 0.540 | NA | $4.85 \times 10^6$ | $1.74 \times 10^6$ |
| C-5 | 5400 | 107.3 | 100.0 | NA | NA | NA | $7.32 \times 10^6$ | $3.52 \times 10^6$ |
| C-6 | 5733 | 110.7 | 98.1 | NA | NA | NA | $7.17 \times 10^6$ | $3.20 \times 10^6$ |
| C-7 | 2375 | 97.3 | 94.5 | 17.9 | 1.620 | 0.140 | $2.81 \times 10^5$ | $7.56 \times 10^4$ |
| C-8 | 3583 | 98.8 | 94.4 | 20.0 | 1.730 | 0.200 | $3.20 \times 10^5$ | $8.91 \times 10^4$ |
| C-9 | 1279 | 93.2 | 90.1 | 12.0 | 1.420 | 0.110 | $2.06 \times 10^5$ | $7.40 \times 10^4$ |
| C-10 | 920 | 91.2 | 91.3 | 12.0 | 1.380 | 0.100 | $1.67 \times 10^5$ | $6.14 \times 10^4$ |
| C-11 | 3700 | 100.7 | 96.2 | 22.0 | 1.620 | 0.200 | $6.84 \times 10^5$ | $1.32 \times 10^5$ |
| C-12 | 3567 | 106.8 | 99.1 | 21.9 | 0.378 | 0.204 | $8.20 \times 10^6$ | $3.96 \times 10^6$ |
| C-13 | 1676 | 100.9 | 96.7 | 21.9 | 1.601 | 0.191 | $6.10 \times 10^5$ | $1.22 \times 10^5$ |
| C-14 | 4583 | 102.3 | 100.0 | 19.9 | 1.640 | 0.215 | $4.18 \times 10^5$ | $1.19 \times 10^5$ |
| C-15 | 5521 | 107.1 | NA | 23.9 | 1.218 | 0.273 | $1.17 \times 10^6$ | $2.97 \times 10^5$ |
| C-16 | 6133 | 107.8 | 101.3 | 23.9 | 1.154 | 0.239 | $1.52 \times 10^6$ | $4.04 \times 10^5$ |

The viscosity and the softening point are measured as mentioned above.

Tx, Tg, Tan σ, mini valley and G' are measured by carrying out a DMA (dynamic mechanical analysis) using a rheometer AR200ex. This analysis makes it possible to obtain a rheometric curve representing the storage modulus G', the loss modulus G" and the loss factor (or damping factor) Tan σ, which is the ratio of G" to G', as a function of the temperature.

Tg is the glass-transition temperature and corresponds to the temperature at which tan σ is maximum.

Tx is the temperature of the cross-over of G' and G".

Mini valley is the minimum value of Tan σ.

NA=not available.

The physical properties of compositions C-2 to C-16 as shown in the table above are close to those of composition C-1, which is a typical HMPSA for nonwoven applications.

Therefore, all the compositions are suitable (from this point of view) to be used as an HMPSA in nonwoven applications.

The invention claimed is:

1. A hot-melt pressure sensitive adhesive composition comprising at least one styrenic block copolymer, at least one tackifying resin, at least one mineral oil and from 4 to 15% by weight of at least one wax selected from the group consisting of paraffin waxes, Fischer-Tropsch waxes, ethylene-vinyl acetate waxes and any mixture thereof, based on the total weight of the hot-melt pressure sensitive adhesive composition.

2. The hot-melt pressure sensitive adhesive composition of claim 1, wherein the at least one wax has a congealing point higher than or equal to 55° C.

3. The hot-melt pressure sensitive adhesive composition of claim 1, wherein the at least one styrenic block copolymer is a styrene-butadiene-styrene copolymer, optionally in combination with a styrene-butadiene diblock copolymer, a styrene-isoprene-styrene copolymer, optionally in combination with a styrene-isoprene diblock copolymer, a styrene-ethylene-butylene-styrene copolymer, a styrene-butadiene-butylene-styrene copolymer, a styrene-ethylene-propylene-styrene copolymer or any mixture thereof.

4. The hot-melt pressure sensitive adhesive composition of claim 1, wherein the amount of the at least one styrenic block copolymer is from 10 to 40% by weight based on the total weight of the composition.

5. The hot-melt pressure sensitive adhesive composition of claim 1, wherein the at least one tackifying resin is selected from the group consisting of natural and modified rosins, glycerol and pentaerythritol esters of natural and modified rosins, polyterpene resins, phenolic-modified terpene resins, aliphatic petroleum hydrocarbon resins having a Ring and Ball softening point of from about 60° C. to 140° C. and resulting from the polymerization of C5-hydrocarbon monomers, their hydrogenated derivatives, aromatic petroleum hydrocarbons resins having a Ring and Ball softening point of from about 60° C. to 140° C. and resulting from the polymerization of C9-hydrocarbon monomers, their hydrogenated derivatives, aliphatic petroleum resins, wherein aliphatic petroleum resins include cycloaliphatic petroleum resins, and/or aromatic petroleum resins (C5/C9) having a Ring and Ball softening point of from about 60° C. to 140° C. and resulting from the polymerization of C5/C9-hydrocarbon monomers, their hydrogenated derivatives and any mixture thereof.

6. The hot-melt pressure sensitive adhesive composition of claim 1, wherein the amount of the at least one tackifying resin is from 30 to 70% by weight based on the total weight of the composition.

7. The hot-melt pressure sensitive adhesive composition of claim 1, wherein the at least one mineral oil comprises a naphthenic oil and/or a paraffinic oil.

8. The hot-melt pressure sensitive adhesive composition of claim 1, wherein the amount of the at least one mineral oil is from 5 to 30% by weight based on the total weight of the composition.

9. The hot-melt pressure sensitive adhesive composition of claim 1, further comprising one or more additives selected from the group consisting of antioxidants, fillers, surfactants, colorants, dyes, pigments, ultraviolet light stabilizers, fluorescent agents, pH indicators, rheology modifiers, crosslinking agents, and endblock reinforcing resins.

10. An article comprising at least one interior or exterior surface coated with the hot-melt pressure sensitive adhesive composition of claim 1.

11. The article of claim 10, wherein the interior or exterior surface is a nonwoven surface.

12. The article of claim 11, wherein the nonwoven surface comprises polypropylene, polyethylene, polyethylene terephthalate, cotton, bamboo, silk or polylactic acid.

13. The article of claim 10, wherein the article is a disposable diaper, disposable training pants, a disposable adult incontinent pad or brief, a disposable feminine sanitary napkin or pad.

14. A surface coating comprising the hot-melt pressure sensitive adhesive composition of claim 1.

15. The surface coating of claim 14, wherein the surface is a nonwoven surface.

16. The surface coating of claim 15, wherein the nonwoven surface comprises a part of an article selected from the group consisting of disposable diapers, disposable training pants, disposable adult incontinent pads or briefs and disposable feminine sanitary napkins and pads.

17. A process for preparing the hot-melt pressure sensitive adhesive composition of claim 1, comprising mixing the at least one styrenic block copolymer, the at least one tackifying resin, the at least one mineral oil and the at least one wax, in the molten state.

\* \* \* \* \*